United States Patent [19]

D'Silva

[11] Patent Number: 5,018,945

[45] Date of Patent: May 28, 1991

[54] ACCURATE PERISTALTIC PUMP

[75] Inventor: Edmund D. D'Silva, Highland Park, Ill.

[73] Assignee: Baxter International Inc., Deerfield, Ill.

[21] Appl. No.: 451,269

[22] Filed: Dec. 14, 1989

[51] Int. Cl.$^5$ .................... F04B 43/12; F04B 49/00
[52] U.S. Cl. ...................................... 417/12; 417/45; 417/53; 417/474; 604/153
[58] Field of Search .................. 417/12, 44, 45, 53, 417/474–477; 604/151, 153

[56] References Cited

U.S. PATENT DOCUMENTS

| | | |
|---|---|---|
| 3,582,234 | 6/1971 | Isreeli et al. . |
| 4,205,238 | 5/1980 | Shim et al. . |
| 4,210,138 | 7/1980 | Jess et al. . |
| 4,213,345 | 7/1980 | Shim . |
| 4,217,993 | 8/1980 | Jess et al. . |
| 4,227,420 | 10/1980 | Lamadrid . |
| 4,231,707 | 11/1980 | Tokorozawa et al. ............... 417/12 |
| 4,233,549 | 11/1980 | Dighe . |
| 4,254,460 | 3/1981 | Achter et al. . |
| 4,299,218 | 11/1981 | Knigge et al. . |
| 4,299,541 | 11/1981 | Ohara et al. .......................... 417/12 |
| 4,346,705 | 8/1982 | Pekkarinen et al. . |
| 4,373,525 | 2/1983 | Kobayashi ....................... 417/474 X |
| 4,394,862 | 7/1983 | Shim . |
| 4,488,700 | 12/1984 | Nakamura et al. . |
| 4,554,492 | 11/1985 | Karpowicz et al. . |
| 4,604,034 | 8/1986 | Wheeldon et al. ................ 417/53 X |
| 4,604,166 | 8/1986 | Weinberg et al. . |
| 4,617,014 | 10/1986 | Cannon et al. . |
| 4,648,869 | 3/1987 | Bobo, Jr. . |
| 4,690,673 | 9/1987 | Bloomquist . |
| 4,692,145 | 9/1987 | Weyant . |
| 4,702,675 | 10/1987 | Aldrovandi et al. ............ 417/477 X |
| 4,715,786 | 12/1987 | Wolff et al. ........................ 417/45 X |
| 4,725,205 | 2/1988 | Cannon et al. . |
| 4,731,057 | 3/1988 | Tanaka et al. . |
| 4,785,799 | 11/1988 | Schoon et al. . |
| 4,846,792 | 7/1989 | Bobo, Jr. et al. . |

Primary Examiner—Leonard E. Smith
Assistant Examiner—Eugene L. Szczecina, Jr.
Attorney, Agent, or Firm—Paul E. Schaafsma; Paul C. Flattery; Bradford R. L. Price

[57] ABSTRACT

A method and device are provided for infusing a fluid into a patient via a tubing. A peristaltic pumping apparatus is provided which applies a pumping action to the tubing. A linear variable differential transformer measures the diameter of the tubing subject to the pumping action. The diameter of the tubing is measured at various times and changes in the diameter of the tubing are utilized to adjust the pumping action on the tubing.

16 Claims, 5 Drawing Sheets

ACCURATE PERISTALTIC PUMP

FIELD OF THE INVENTION

The present invention relates in general to peristaltic pumps and in particular to improving the accuracy of such peristaltic pumps.

BACKGROUND OF THE INVENTION

Administration of intravenous fluids to a patient is well known in the art. Typically, a solution such as saline, glucose or electrolyte in a glass or flexible container is fed to a patient's venous access site via a length of flexible plastic tubing such as polyvinyl chloride (PVC) tubing. The rate of flow of the fluid is controlled by a roller clamp which is adjusted to restrict the flow lumen of the tubing until the desired flow rate is obtained.

Flow from the container to the patient may also be regulated by means other than a roller clamp. It is becoming more and more common to use an electronically controlled pump. One type of pump that is used for intravenous fluid administration is a peristaltic-type pump.

Use of peristaltic pumping action is particularly well suited for the medical field. This is because peristaltic pumping action can be applied externally of the tubing carrying the intravenous fluid. This maintains the sterile condition of the intravenous fluid within the tubing while imparting fluid propulsion on the fluid. The peristaltic pumping action can also be applied at any point on the tubing.

A peristaltic pump is also particularly useful as the pump can be applied at any point on tubing to provide fluid propulsion. In a common type of peristaltic pump used in the medical field, a driving motor is connected to an array of cams angularly spaced from each other. The cams in turn drive cam followers connected to corresponding pressure fingers. These elements cooperate to impart a linear wave motion on the pressure fingers. A pressure plate is secured juxtaposed and spaced from the pressure fingers. The pressure plate holds the tubing against the reciprocating pressure fingers to impart the wave motion on the tubing to propel the fluid.

A problem associated with peristaltic pumps of this type is that over long periods of infusion such as 24 hours or longer, the diameter of the tubing can vary. If the diameter of the tube changes, the flow rate will also change. This variance can result from a change in the temperature of the fluid being infused, a change in the air temperature in the room, a variance in the downstream pressure from the patient resistance, a variance in the upstream pressure from the source of fluid, and a breakdown in the resiliency in the tubing subject to the pumping action.

Particularly important in accounting for changes in the flow rate of the fluid is the breakdown in the tubing resiliency. This results in a flattening of the tubing subject to the pumping action. This flattening results in a drop in the amount of fluid subject to the pumping action which in turn results in a drop in the fluid delivery rate over time. This can be referred to as hysteresis.

Hysteresis can be solved manually by changing the orientation of the tubing, thereby exposing a different length of tubing to the pumping action. This solution is not satisfactory for several reasons. Initially, moving the tubing results in an interruption of the fluid flow. Additionally, a nurse or other hospital worker must take the time to move the tubing.

Another solution is to speed up the rate of the motor during infusion according to a predetermined schedule. While this will result in an improved delivery accuracy, it is also not entirely satisfactory for several reasons. Initially, small variances in the tubing width can result in a different infusion rate from one segment of tubing to another. In addition, each segment of tubing exhibits a different rate of breakdown in resiliency. Further, if the tubing is replaced or the orientation of the pressure fingers is changed on the same tubing, the predetermined schedule of rate increase may actually result in a decrease in accuracy. Finally, this system fails to account for other causes of diameter variance.

What is thus needed is a device which improves the accuracy of the fluid flow of a peristaltic pump by taking into account the various factors which change infusion rates. The present invention provides such a device.

SUMMARY OF THE INVENTION

The present invention provides a method and apparatus for improving the accuracy of fluid flow in a peristaltic pump. A method is provided for changing the speed of the driving motor as a function of changes in the minor diameter of the tubing carrying the fluid. The method includes measuring the minor diameter of the tubing, comparing the measurement of the tubing minor diameter with a previous measurement of the minor diameter of the tubing, and changing the motor drive speed as a function of the change in the diameter of the tubing in conjunction with the time elapsed and the selected rate of infusion.

An apparatus is provided to effectuate this method. The apparatus of the present invention includes a standard peristaltic pumping apparatus driven by a drive motor. Juxtaposed opposite the pressure fingers is a pressure plate which secures the tubing between the pressure plate and the pressure fingers.

The device includes means for measuring the diameter of the tubing, which in a preferred embodiment is a linear variable differential transformer (LVDT) mounted in the pressure plate of the peristaltic pump juxtaposed to the pressure fingers. The measuring means includes an output which is fed into a microprocessing means. The microprocessing means includes a comparator means. The comparator means compares the minor diameter of the tubing as measured at various time intervals to a previous reading of the tubing minor diameter derived from the measuring means. The microprocessor regulates the speed of the driving motor, changing the driving speed as a function of the change in minor diameter of the tubing in conjunction with the elapsed time and the selected rate of infusion.

DETAILED DESCRIPTION OF A PREFERRED EMBODIMENT

Figure 1:
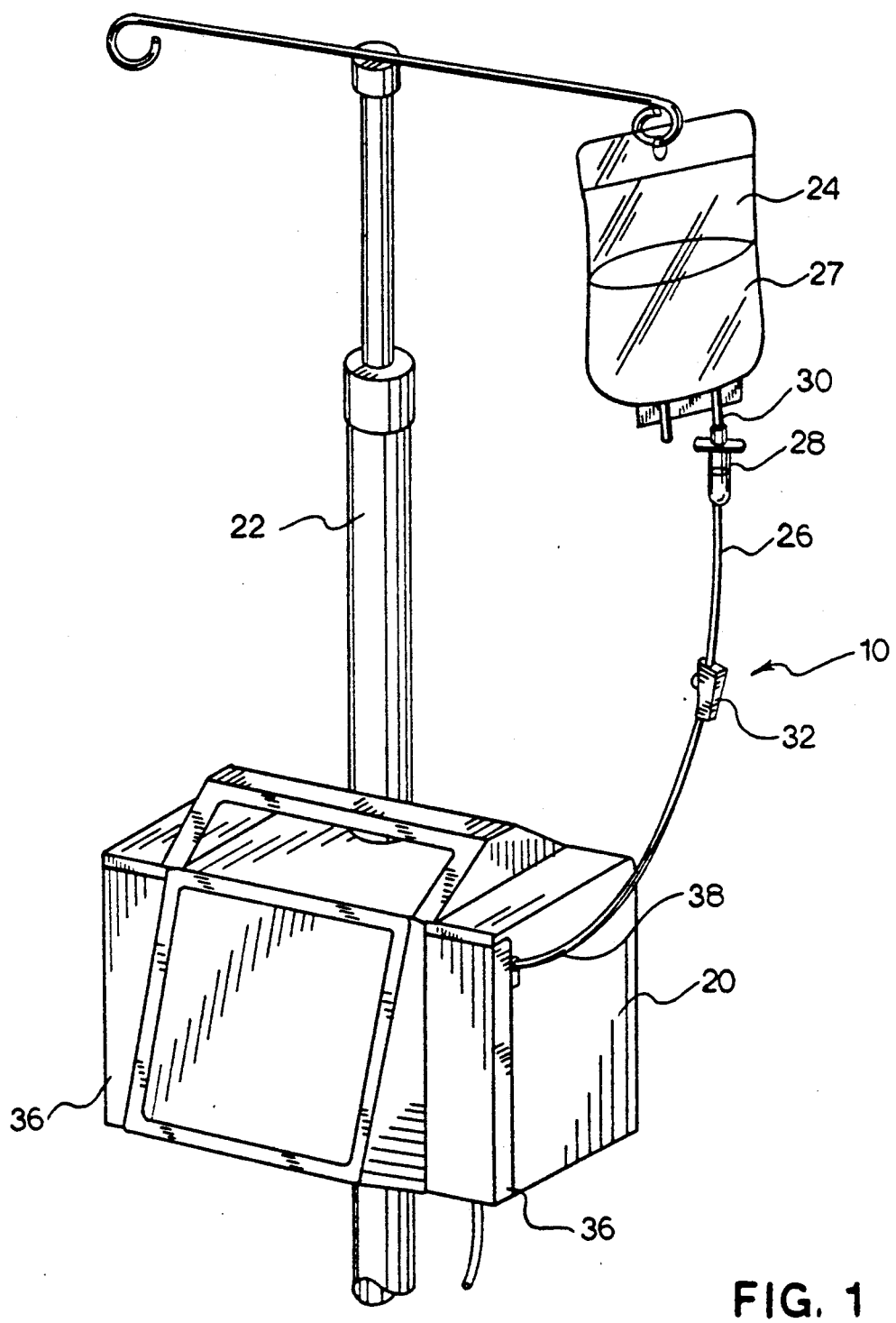
FIG. 1 is a perspective view of an intravenous pump set utilizing a peristaltic pumping apparatus.

FIG. 1 is an illustration of an intravenous administration set up using a pump and a source of intravenous fluid such as a flexible container. Pump 20, which is provided with a pump operating mechanism and operating electronics (not shown), is mounted on an I.V. stand 22 which also serves as a support for the intravenous fluid container 24. Container 24, which typically contains a fluid 26 such as saline that is continually administered, is also suspended from stand 22.

An administration set 10 provides a flow path from container 24 to the patient via pump 20. Set 10 includes a segment of flexible plastic tubing 26 such as polyvinyl chloride (PVC) tubing.

Tubing 26 at its proximal end is attached to a drip chamber 28 that in turn is attached via a spike (not shown) to an outlet port 30 of container 24. A clamping means such as a roller clamp 32 is positioned on tubing 26 at a point between pump 20 and container 24. Tubing 26 has connected at its distal end means for connecting set 10 to a vein access device, such as a catheter or needle (not shown).

Pump 20 includes a hinged door 36 which covers the peristaltic pumping apparatus hardware. To set up pump 20, door 36 is opened, tubing 26 is inserted into the peristaltic pumping apparatus as described in detail below, door 36 is closed, and pump 20 is activated. Pump 20 also defines apertures 38 at the upper and lower (not shown) peripheries of the door 36 through which the tubing 26 extends when door 36 is closed.

While the embodiment depicted in FIG. 1 includes a dual drive peristaltic pump, the present invention contemplates use of any number of pump drives in a single peristaltic pump.

Figure 2:
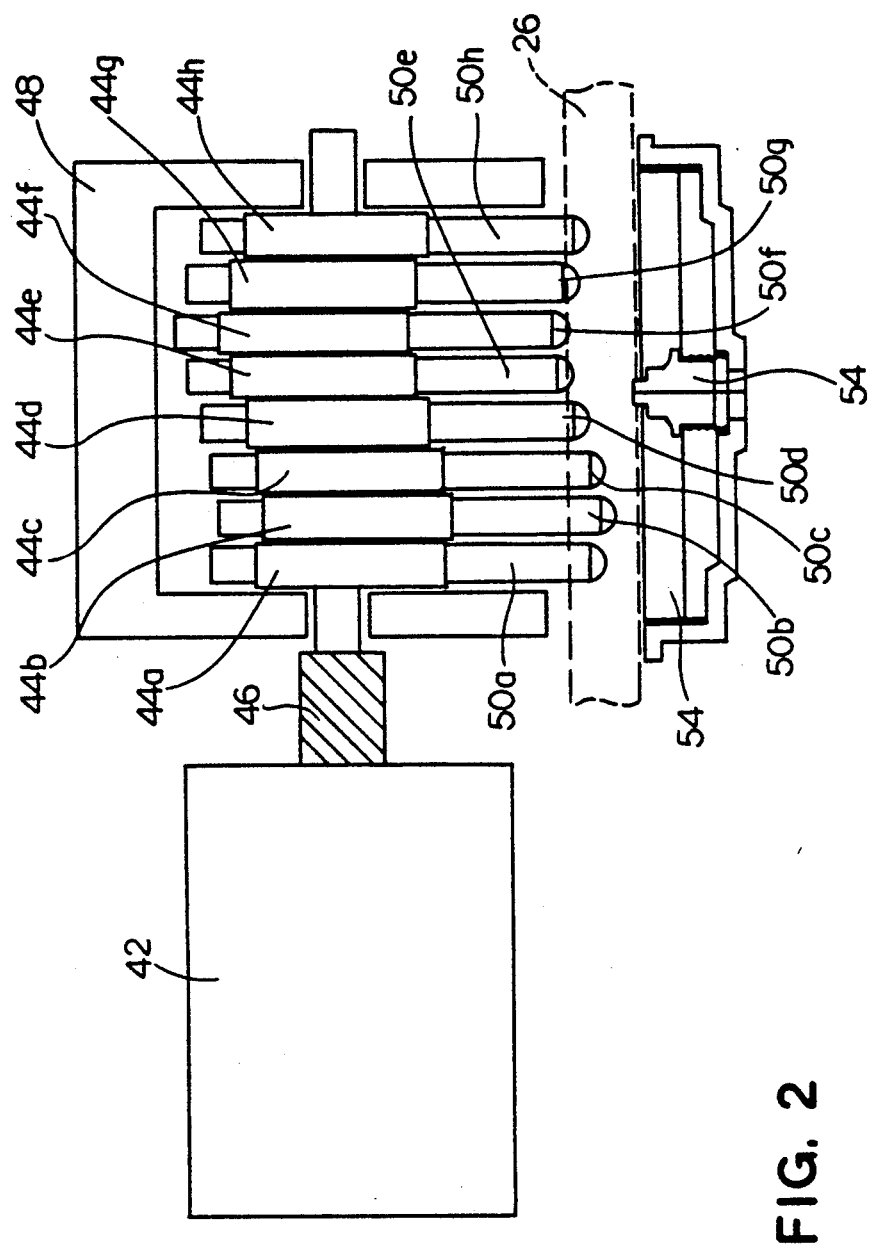
FIG. 2 is a schematic of a peristaltic pumping apparatus in accordance with the principles of the present invention.

Referring now to FIG. 2, a general schematic of a peristaltic pumping apparatus is seen. A driving motor 42 is connected to a plurality of cams 44$a$–$h$ via a drive shaft 46. While in the embodiment depicted in FIG. 2 eight cams are utilized, any number of cams are contemplated in the present invention. Each cam 44 is angularly displaced from the adjacent cam. The plurality of angularly displaced cams 44$a$–$h$ are journaled in housing 48 which enables rotation in conjunction with the drive shaft 46.

A plurality of reciprocating pressure fingers 50$a$–$h$ are provided, the number of which correspond to the number of cams 44$a$–$h$. Each pressure finger 50 cooperates with a corresponding cam 44 by acting as a cam follower to reciprocally drive the pressure finger 50. The rotational movement of the drive shaft 46 is thus converted into a linear wave movement of the plurality of reciprocating pressure fingers 50$a$–$h$.

A pressure plate 54 is provided located juxtaposed to the pressure fingers 50$a$–$h$ and extending parallel to the axis of the cams. Tubing 26 is contained between the pressure fingers 50 and the pressure plate 54. Fluid propulsion is effectuated by the pressure fingers 50$a$–$h$ squeezing the tubing 26 in the linear wave movement imparted by the angular orientation of the cams 44$a$–$h$.

The present device further includes means for measuring the diameter of the tubing 26 positioned juxtaposed to the pressure fingers 50. In a preferred embodiment, the measuring means is a linear variable differential transformer (LVDT) 54 as known in the art. Such linear variable differential transformer (LVDT) 54 device measures and converts linear displacement into an analog signal. However, use of other types of measuring means such as, for example, optical, ultrasonic, hydraulic, mechanical, or electrical, are also contemplated by the present invention.

Figure 3:
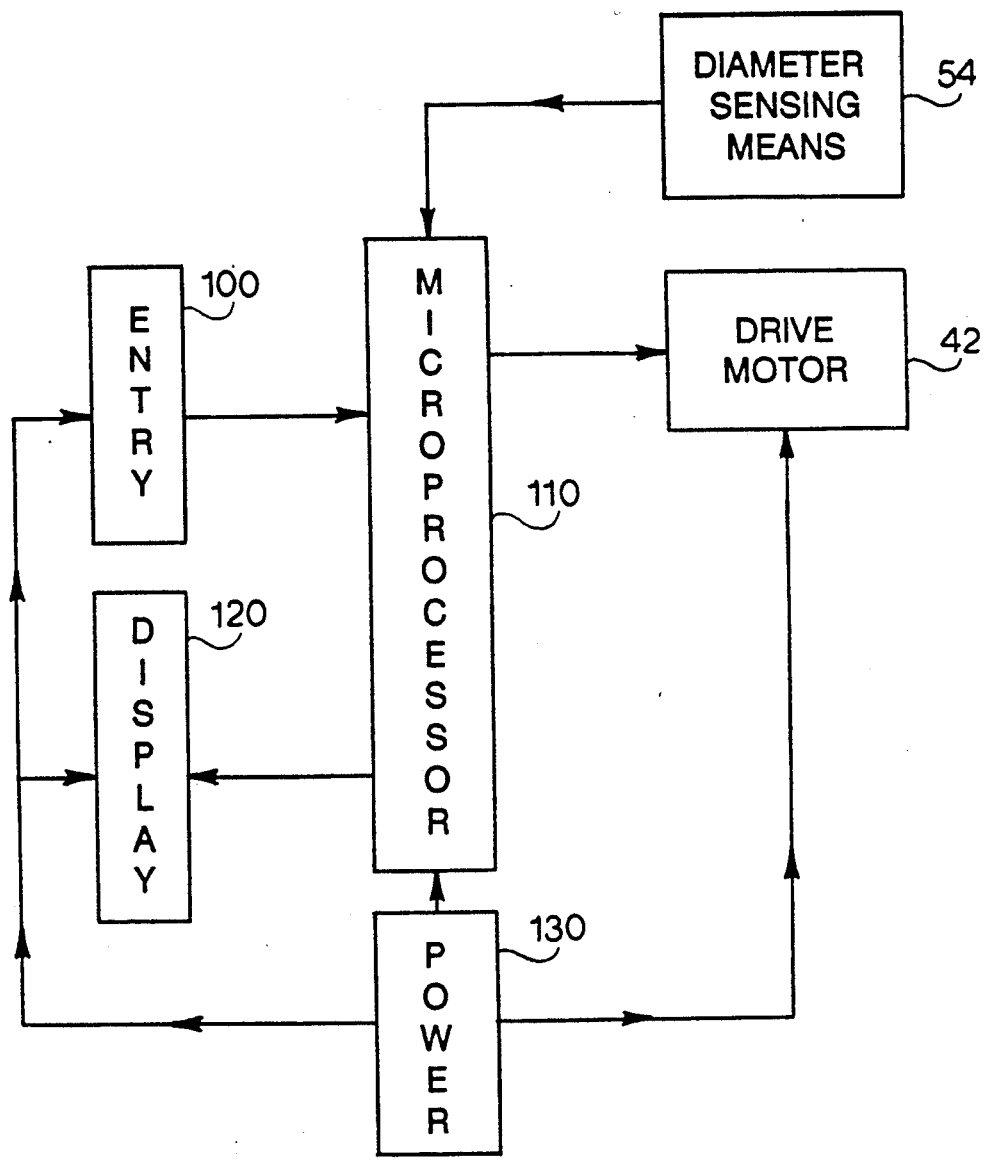
FIG. 3 is a block diagram of the operating electronics of a peristaltic pumping apparatus.

Referring now to FIG. 3, a schematic block diagram of the control circuit of a device in accordance with the principles of the present invention is shown. A standard entry keyboard 100 as known in the art is provided which is used to input user controlled parameters of the infusion, such as, for example, the flow rate of infusion, the time of infusion, etc., into a microprocessor 110. The user controlled parameters are stored in random access memory (RAM) provided in the microprocessor 110. A standard display 120 is provided as known in the art which displays the users' chosen parameters. The drive motor 42 is controlled via a driving signal generated by the microprocessor 110. A power source 130 provides power to the various components.

It has been found that a high degree of accuracy in correcting the flow rate of a peristaltic pump infusion device can be attained by utilizing three variables: time, flow rate, and change of tubing diameter. Thus, in a preferred embodiment, the adjustment to the driving motor is made as a function of time of infusion (t), the rate of infusion (R), and the change in tubing diameter ($\Delta D$), as seen below:

$$A = f(t) + f(\Delta D) + f(R)$$

The rate of infusion is preselected by the user or inputted via keyboard into the microprocessor. The time of infusion is measured via means provided in the microprocessor. The change in tubing diameter is provided to the microprocessor as measured by means for measuring the external diameter of tubing.

In the presently preferred embodiment, the means for measuring the external diameter of the tubing, as previously discussed, is a linear variable differential transformer (LVDT) 54. The analog signal from the linear variable differential transformer (LVDT) is entered into the microprocessor 110 random access memory (RAM) to be utilized in generating the driving signal, as will be discussed in detail below.

Figure 4:
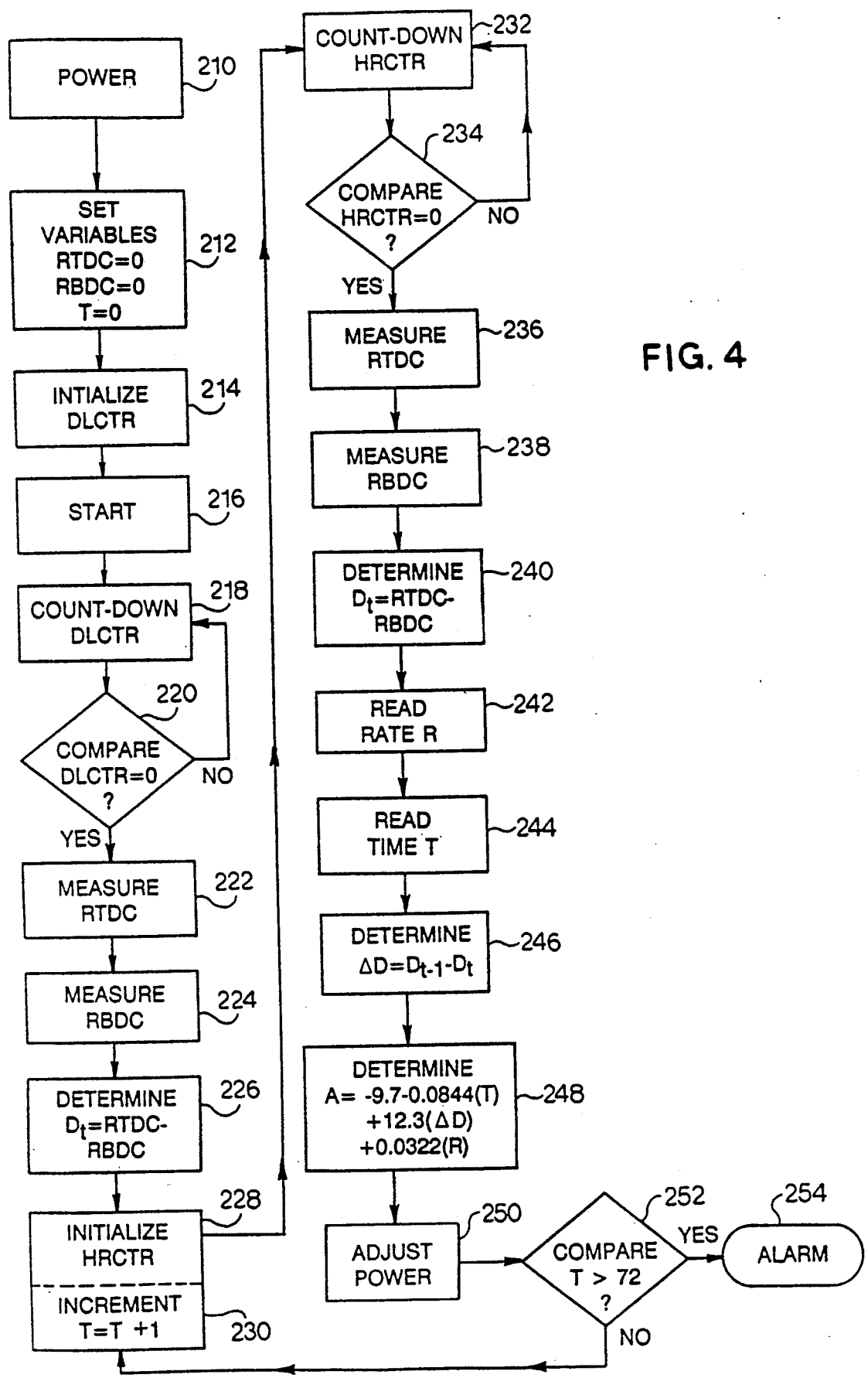
FIG. 4 is a flow chart of a method of operation in accordance with the principles of the present invention.

Referring to FIG. 4, a flow diagram of a method of infusion in accordance with the present invention is seen. After power 210 to the microprocessor is turned on by the user via the entry keyboard, the variables RTDC, RBDC, as well as the time variable T, are set 212 to zero while an initial delay period counter DLCTR is initialized 214 to a predetermined number. The initial delay is provided so that initial transients in the motor driving system as well as in the tubing resiliency behavior are eliminated. In the preferred embodiment, the delay period can be five (5) minutes.

After the infusion is started 216 by the user via keyboard input, the delay counter 218 proceeds to count down. The delay counter is then compared 220 to the set parameter zero. When the delay period has passed, or DLCTR is zero, an initial diameter reading of the tubing is taken by the linear variable differential transformer (LVDT).

To determine the initial diameter reading, a measurement is taken at the top dead center 222 of the pump cycle, which is assigned the variable RTDC, as well as at the bottom dead center 224 of the pump cycle, which is assigned the variable RBDC. The top dead center refers to the external diameter of the portion of the tubing to which the peristaltic action is applied when no pressure fingers are contacting the tubing. The bottom dead center refers to the external diameter of the portion of the tubing to which the peristaltic action is applied when that portion of the tubing is occluded. While it is the internal diameter of this tubing that effects the flow rate of the fluid and the external diameter of the tubing is being measured, the change in tubing thickness over time is negligible. Thus, the difference in the external diameter of the tubing at top dead center and bottom dead center gives the change in minor diameter of the tubing internally and externally. Additionally, as the resiliency of the tubing breaks down, the initially circular tubing slowly changes from a circle to an ellipse to an oval. The minor diameter of the tubing is measured as the smallest diameter of the tubing as the circular tubing slowly changes from a circle to an ellipse to an oval. The difference between these readings $D_t$ is determined 226 and is stored in microprocessor random access memory (RAM).

After the minor diameter $D_t$ reading of the tube is determined, countdown variable HRCTR is initialized 228 to a predetermined time period after which a new measurement of the minor diameter of the tubing will be made. In the preferred embodiment, this countdown variable is set at one hour. Additionally, time variable T is incremented 230 by one count, which keeps tabs on the number of time periods which have passed.

Immediately upon initialization of countdown variable HRCTR the microprocessor begins counting down 232. The countdown variable HRCTR is then compared 234 to the set parameter zero. When the countdown variable HRCTR equals zero, a second diameter reading of the tube is taken by the linear variable differential transformer (LVDT). Again, a reading is taken at top dead center RTDC 236 and at the bottom dead center RBDC 238. The bottom dead center reading RBDC is subtracted from the top dead center reading RTDC to determine 240 a second minor diameter reading $D_{t+1}$ of the tube.

As previously discussed, the adjustment of the driving motor is made as a function of time of infusion, rate of infusion, and the change in diameter. Thus, the rate of infusion as preselected by the user is read 242 from the random access memory (RAM) while the time variable T is utilized for the time of infusion.

The change in tube diameter $\Delta D$ is determined 246 by taking the difference between the initial diameter $D_t$ measurement of the tube and the second diameter $D_{t+1}$ measurement of the tube. This change $\Delta D$ is then utilized by the microprocessor to determine the rate at which adjustment of the peristaltic pump drive motor is needed to maintain a relatively constant infusion rate. In a preferred embodiment, this adjustment is determined 248 in accordance with the formula $$A/100 = -9.7 - 0.0844(T) + 12.3(\Delta D) + 0.0322(R)$$

wherein
A = adjustment (percentage change)
T = time variable (in hours)
$\Delta D$ = change in tube diameter (in inches)
R = flow rate (in ml/hr).

It has been found that utilizing this formula provides a great degree of accuracy while utilizing a relatively small amount of microprocessor memory.

The variable A is then used to adjust 250 the speed of the driving motor.

After the motor speed adjustment has been made, the time variable T is compared 252 with an upper time limit which is determined as the length of time after which the tube should be replaced. In a preferred embodiment, upper time limit can be about seventy-two (72) hours. If the time variable T exceeds the upper time limit, an alarm 254 is sounded in the pump display instructing the user to replace the IV set. If the upper time limit is not exceeded, the count down variable HRCTR is again initialized 228 and the time variable T is incremented 230 by one for an additional tube diameter measurement $D_{(t+2)}$.

Once again, immediately upon initialization of countdown variable HRCTR, the microprocessor begins counting down 232. When HRCTR again equals zero 234, a new diameter reading $D_{(t+2)}$ of the tubing is taken by linear variable differential transformer 236, 238. This reading is again the difference 240 of the top dead center reading RTDC and the bottom dead center reading RBDC.

The flow rate R is again read 242. The change in tube diameter $\Delta D$ is determined 246 by taking the difference between the previous diameter reading $D_{(t+1)}$ of the tubing and the new diameter reading $D_{(t+2)}$ of the tubing. Generally, the change in tubing diameter $\Delta D$ at any time t is calculated as follows:

$$\Delta D = D_{t-1} - D_t$$

The change is again determined 248 by the microprocessor and the speed of the driving motor is adjusted 250 to maintain a constant infusion rate in accordance with the preferred formula. This process is repeated until the time variable T exceeds 252 the upper time limit and the alarm 254 is sounded to replace the intravenous set.

Figure 5:
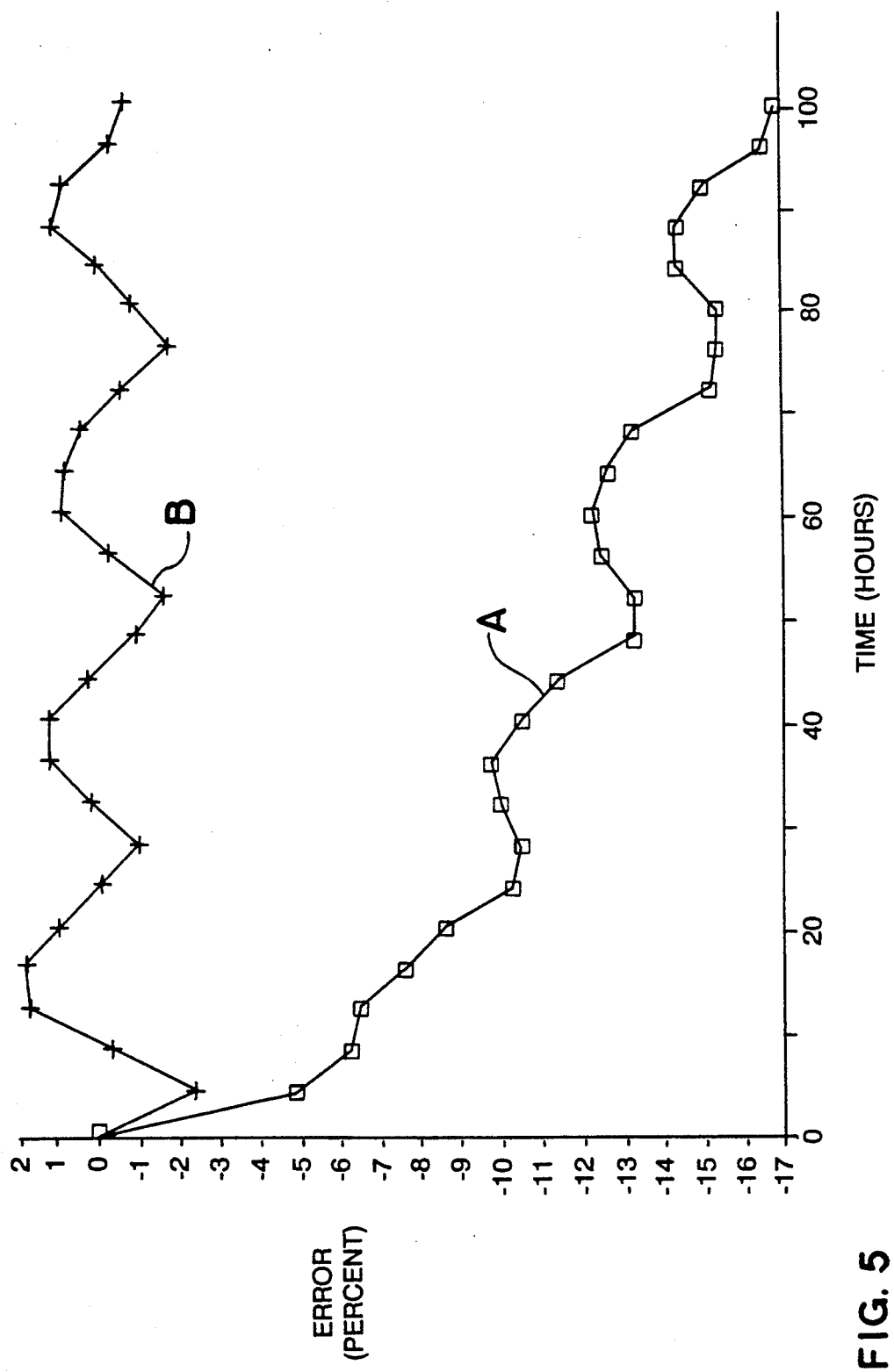
FIG. 5 is a graph showing the improved flow rate of a peristaltic pump utilizing the principles of the present invention over time.

Referring to FIG. 5, a graph is shown demonstrating the increase in accuracy of a peristaltic pump in accordance with the present invention. The graph depicts the percentage error in flow rate of a peristaltic pump as a function of time of infusion in hours. Line A, a standard IV tubing available as a set from Baxter Healthcare Corporation, Deerfield, Ill. 60015, was tracked for 100 hours at a flow rate of 70 ml/hr. utilizing a standard prior art pump. Line B shows the rate of infusion as calculated in accordance with the preferred formula of the present invention. As is seen, the improvement in accuracy decay in this example is seen with a resultant accuracy drop of about 1%.

It should be understood that various changes and modifications to the preferred embodiment described herein will be apparent to those skilled in the art. For example, the principles of the present invention can also apply to rotary type peristaltic pumps. Such changes and modifications can be made without departing from the spirit and scope of the present invention without diminishing its attendant advantages. It is therefore intended that such changes and modifications be covered by the appended claims.

What is claimed is:

1. A method for infusing a fluid from a source of fluid to a patient through tubing comprising:
    (1) applying external pumping action to the tubing;
    (2) measuring a diameter of the tubing subject to the pumping action after passage of a period of time;

(3) comparing the diameter of the tubing after the passage of a period of time with a previous diameter of the tubing; and (4) adjusting the rate of the pumping action to compensate for any change in diameter of the tubing to maintain an approximately constant flow rate of infusion.

2. The method of claim 1 further including repeating steps (2), (3) and (4) for a multiplicity of periods of time.

3. The method of claim 1 wherein the external diameter of the tubing is measured.

4. The method of claim 1 wherein the pumping action is peristaltic.

5. The method of claim 1 wherein the adjustment to the rate of pumping action is further made as a function of the time of infusion and the rate of infusion.

6. The method of claim 5 wherein the adjustment to the rate of pumping action is made in accordance with the formula:

$$A/100 = -9.7 - 0.0844(T) + 12.3(\Delta D) + 0.0322(R)$$

where A is the percent adjustment in the motor speed, T is the time of infusion in hours, $\Delta D$ is the change in tube diameter in inches, and R is the rate of infusion in millimeters per hour.

7. A device for infusing fluid from a source of fluid through tubing to a patient comprising:
   means for applying a pumping action on the exterior of the tubing to provide fluid propulsion;
   means for measuring the diameter of the tubing subject to the pumping means;
   means for storing a plurality of diameter measurements of the tubing;
   means for comparing the diameter measurements of the tubing to determine changes in the tubing diameter; and
   means for adjusting the rate of the pumping action on the exterior of the tubing to compensate for any change in the tubing diameter to maintain an approximately constant flow rate of infusion.

8. The device of claim 7 wherein the means for applying a pumping action is a peristaltic pump.

9. The device of claim 7 wherein the means for measuring the diameter of the tubing is a linear variable differential transformer.

10. The device of claim 7 wherein the means for storing and means for comparing is a microprocessor.

11. The device of claim 7 wherein the means for adjusting includes means for changing the speed of the pumping means.

12. A pump for infusing fluid into a patient via a tube comprising:
   a peristaltic pumping apparatus applied externally to the tube;
   a driving motor for driving the peristaltic pumping apparatus at a speed;
   a pressure plate provided juxtaposed to the peristaltic pumping apparatus, the tubing being secured between the pressure plate and the peristaltic pumping apparatus;
   means provided in the pressure plate for measuring the diameter of the tubing to which the peristaltic pumping apparatus is applied; and
   means for comparing the measurements of the tubing diameter to determine changes in diameter of the tubing; and
   means for regulating the speed of the driving motor to compensate for any change in tubing diameter to maintain an approximately constant flow rate of infusion.

13. The pump of claim 12 wherein the comparing means is a microprocessor.

14. The pump of claim 12 wherein the regulating means is a microprocessor.

15. The pump of claim 12 wherein the peristaltic pumping apparatus includes an array of cams secured to the driving motor, the array of cams driving a plurality of cooperating pressure fingers.

16. The pump of claim 12 wherein the means for measuring is a linear variable differential transformer.

* * * * *